United States Patent [19]

Weijand

[11] Patent Number: 5,540,729
[45] Date of Patent: Jul. 30, 1996

[54] MOVEMENT POWERED MEDICAL PULSE GENERATOR HAVING A FULL-WAVE RECTIFIER WITH DYNAMIC BIAS

[75] Inventor: Koen J. Weijand, Hoensbroek, Netherlands

[73] Assignee: Medtronic, Inc., Minneapolis, Minn.

[21] Appl. No.: 359,237

[22] Filed: Dec. 19, 1994

[51] Int. Cl.⁶ .................................................. A61N 1/362
[52] U.S. Cl. ............................................................ 607/35
[58] Field of Search ................................... 607/19, 33, 34, 607/35

[56] References Cited

U.S. PATENT DOCUMENTS

| | | | |
|---|---|---|---|
| 3,681,674 | 8/1972 | Terry, Jr. ........................................ | 321/2 |
| 3,923,060 | 12/1975 | Ellinwood, Jr. . | |
| 3,943,936 | 3/1976 | Rasor et al. . | |
| 4,015,609 | 4/1977 | Mensink et al. . | |
| 4,031,899 | 6/1977 | Renirie . | |
| 4,044,775 | 8/1977 | McNichols . | |
| 4,245,640 | 1/1981 | Hunt . | |
| 4,615,625 | 10/1986 | Moriya ..................................... | 368/156 |
| 4,644,246 | 2/1987 | Knapen ..................................... | 329/21 |
| 4,788,669 | 11/1988 | Kamiyama ................................ | 368/80 |
| 4,908,808 | 3/1990 | Knapen et al. ........................... | 368/157 |
| 4,910,720 | 3/1990 | Ray et al. ................................. | 368/148 |
| 4,939,707 | 7/1990 | Nagao ....................................... | 368/64 |
| 5,001,685 | 3/1991 | Hayakawa ................................ | 368/204 |
| 5,271,395 | 12/1993 | Wahlstrand et al. ..................... | 607/9 |
| 5,278,806 | 1/1994 | Affolter ..................................... | 368/204 |

OTHER PUBLICATIONS

*MOSPOWER Applications Handbook*, Rudolf P. Severns and Jack Armijos, pp. 5–91 through 5–92.

"A Study of the Automatic Generating System (3)–Improvement of the Total System Performance," CEC 92, Session: Chronometrie–Mouvements, Et Produits Termines I, Communication 33, pp. 159–162.1

*Primary Examiner*—William E. Kamm
*Assistant Examiner*—Scott M. Getzow
*Attorney, Agent, or Firm*—Michael J. Jaro; Harold R. Patton

[57] ABSTRACT

The present invention concerns pulse generators which are powered through movement. Such devices include both implantable medical devices, such as cardiac pacemakers, as well as wristwatches. The present invention particularly concerns a pulse generator which features a full-wave rectifier circuit which has dynamic bias. The full-wave rectifier circuit is implemented using four field-effect transistors (FETs) operable to selectively establish the paths between first and second input terminals and first and second output terminals thereof. Alternating pairs of the diode/FETs are rendered conductive during positive and negative excursions of the input signal to be rectified. Two differential sense amplifiers are associated with two respective ones of the diode/FETs. A dynamic bias circuit is responsive to both positive and negative excursions of the input signal to provide bias current to at least one of the differential sense amplifiers, such that the predetermined threshold amount is substantially less than the threshold of conventional diodes.

1 Claim, 8 Drawing Sheets

MOVEMENT POWERED MEDICAL PULSE GENERATOR HAVING A FULL-WAVE RECTIFIER WITH DYNAMIC BIAS

FIELD OF THE INVENTION

This invention relates generally to pulse generators and in a particular embodiment to a pulse generator having a full-wave rectifier circuit with dynamic bias.

BACKGROUND OF THE INVENTION

The present invention concerns pulse generators which are powered through movement or motion. Typically generators or dynamos which generate power from movement generate the power in the form of an A.C. signal. Most pulse generators, however, require a D.C. power supply. Thus pulse generators which are powered through movement require the A.C. signal to be converted or rectified to a D.C. signal. The present invention particularly concerns pulse generators which feature a full-wave rectifier circuit which has dynamic bias. This circuit may be used in various types of movement powered pulse generators and is particularly useful in an implantable medical device, such as a pacemaker, as well as in a wristwatch.

An A.C. signal in general is an oscillation of voltage having both positive-and negative-going excursions. Rectification in general involves reversing the polarity of the negative-going excursions of the oscillatory signal so that the resultant signal has only positive excursions of voltage.

Previously several types of rectifier circuits have been developed. Among the most well-known types is a "Graetz bridge" rectifier circuit. A Graetz bridge, comprises an interconnection of four diodes. The diodes used in a Graetz bridge and in other well-known types of rectifier circuits may be of the conventional P-N type or the well-known Schottky type, among others.

An "ideal" P-N diode (i.e., the theoretical diode typically used for the purposes of conceptual circuit design) permits current to conduct in only one direction (the "forward" direction) and completely prevents the conduction of current in the opposite ("reverse") direction. In addition, it is often acceptable for the purposes of conceptualizing a circuit to assume that there is no voltage drop across an ideal diode. Actual diodes, however, may not completely prevent reverse current (i.e., there may be some "reverse leakage" through a diode.) Actual diodes also typically have a threshold voltage (sometimes called a "turn-on" voltage) of 0.7 volts or so. This means that a forward-bias voltage of at least 0.7 volts must be applied to the diode before forward conduction of current through the diode will commence, and that when current is being conducted through the diode, there will be a 0.7 volt voltage drop across the diode.

Schottky diodes have a relatively lower threshold voltage as compared with P-N diodes. Schottky diodes, however, also tend to have a relatively higher reverse leakage (sometimes also called self-leakage) as compared with P-N diodes.

In many applications, the threshold voltage and reverse leakage characteristics of either P-N diodes or Schottky diodes have negligible impact upon the performance of the circuits in which they are used. In some circumstances, however, the threshold voltage and reverse leakage behavior of a diode can be critical to the operation of a circuit. This is true, for example, in relatively low voltage applications, such as in circuits powered with a supply voltage on the order of one to three volts or lower. Such circuits are found in such pulse generators as a movement powered medical pulse generator, such as a pacemaker, as well as in a wristwatch.

One method used to overcome the threshold voltage problems of conventional diodes involves continuously biasing the diodes to conduction. This is proposed, for example, in U.S. Pat. No. 4,533,988 to Daly et al., entitled "On-Chip CMOS Bridge Circuit." This solution may be unacceptable, however, for applications in which minimizing power supply current drain is of concern. For example, the operational longevity of battery-powered electronic devices can be adversely affected by the current drain associated with continuous biasing circuitry.

The performance of conventional P-N or Schottky diodes may also present complications in relatively high-frequency applications, such as in rectifiers for rectifying A.C. signals in the kHz or higher frequency range. The above-noted continuous biasing arrangement can sometimes improve the diode frequency response, but again, this may not be acceptable in circumstances where current drain on the power supply must be minimized.

Low-impedance full-bridge rectifiers utilizing field-effect transistors (FETs) have been proposed in the prior art. One such rectifier utilizes two cross-connected N-type FETs and two cross-connected P-type FETe to accomplish full-wave rectification. See, e.g., 1984 Siliconix Inc. MOSPOWER Applications Handbook, pp. 5-91–5-92. Such a configuration, however, is primarily useful only where an input voltage is continuously present.

SUMMARY OF THE INVENTION

The present invention concerns pulse generators which are powered through movement. The present invention particularly concerns a pulse generator which features a full-wave rectifier circuit which has dynamic bias. This circuit may be used in various embodiments of movement powered pulse generators, such as in an implantable medical device, such as a pacemaker, as well as in a wristwatch.

The pulse generator of the present invention uses a full-wave rectifier circuit to rectify a relatively low-voltage signal or a high frequency signal (i.e., in the kHz range or higher) or both. In one embodiment, the full-wave rectifier circuit has four switches, implemented with field-effect transistors (FETe), which are used to selectively establish the current paths necessary to perform rectification of an oscillating input signal. Alternating pairs of the diode/FETs are rendered conductive during positive and negative excursions of the input signal, respectively.

In accordance with one aspect of the present invention, differential sense amplifiers are provided to compare the magnitude of the input signal with the magnitude of the output signal from the rectifier circuit. Each sense amplifier activates one of the diode/FETs when the magnitude of the input signal exceeds the magnitude of the output signal by a predetermined amount, specifically an offset voltage deliberately introduced by a differential sense amplifier.

In accordance with another aspect of the present invention, a dynamic bias circuit is provided which is responsive to both positive and negative excursions of the input signal to provide bias current to the sense amplifiers, such that no bias current is applied when no input signal is present.

In accordance with yet another aspect of the present invention, the dynamic activation of the bias circuitry serves to minimize the current drain of the rectifier circuit, thereby improving the operational characteristics of the rectifier in applications in which power consumption is of concern.

BRIEF DESCRIPTION OF THE DRAWINGS

The foregoing and other aspects of the present invention may perhaps be best appreciated with reference to a detailed description of a specific embodiment of the invention, when read in conjunction with the accompanying drawings, wherein.

The drawings are not necessarily to scale.

DETAILED DESCRIPTION OF THE INVENTION

The present invention concerns pulse generators which are powered through movement. Such devices include both implantable medical devices, such as cardiac pacemakers, as well as wristwatches. In general such devices use the motion or movement of a person to generate power. Typically generators or dynamos which generate power from motion generate the power in the form of an A.C. signal. Most pulse generators, however, require a D.C. power supply. Thus pulse generators which are powered through movement require the A.C. signal to be converted or rectified to a D.C. signal. The present invention particularly concerns a pulse generator which features a full-wave rectifier circuit with dynamic bias.

DETAILED DESCRIPTION OF AN IMPLANTABLE MEDICAL DEVICE FEATURING THE RECTIFIER CIRCUIT OF THE PRESENT INVENTION

Figure 1:
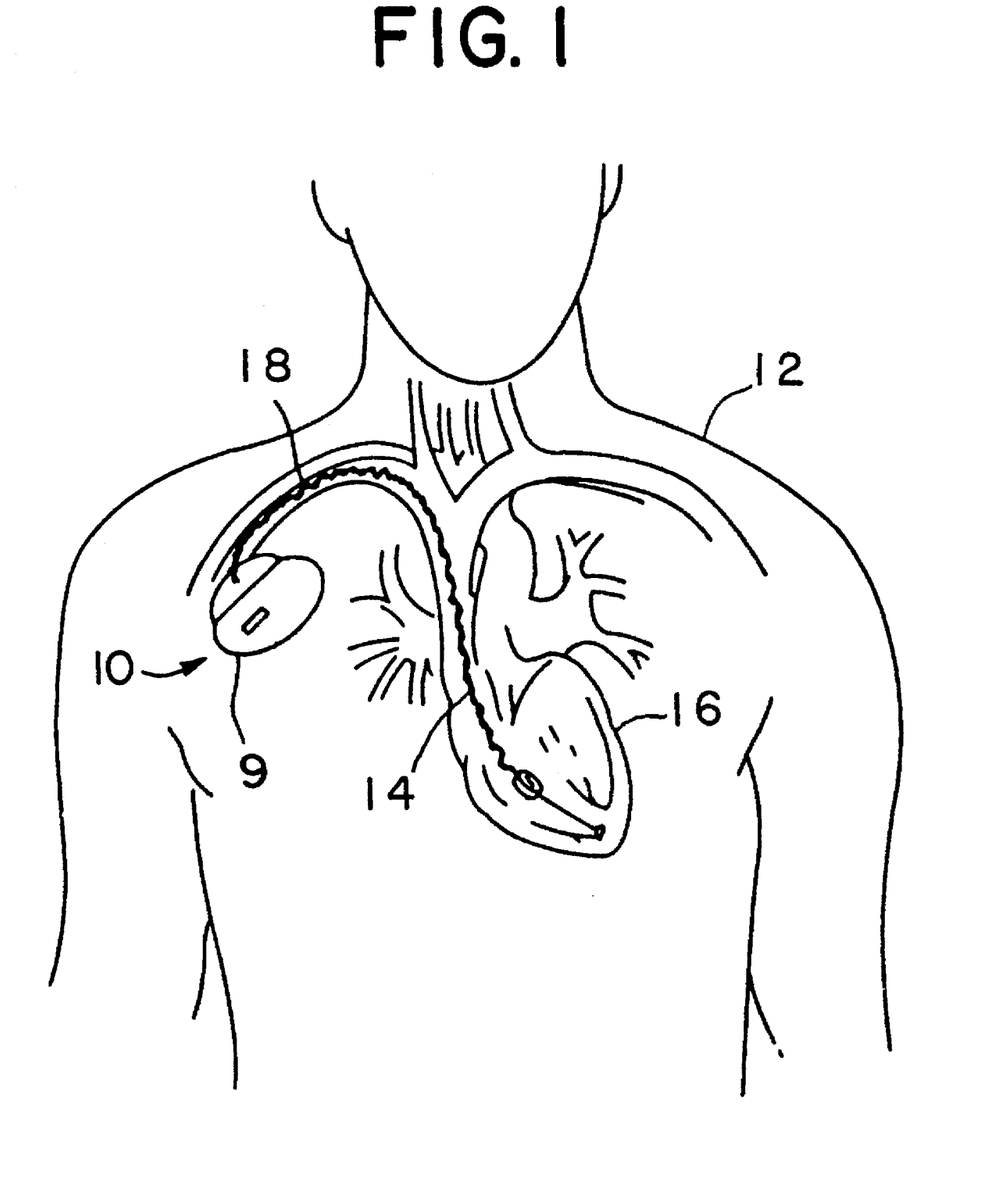
FIG. 1 is a diagram showing the placement in a patient of an implantable pulse generator in accordance with one embodiment of the present invention.

FIG. 1 shows generally an implantable medical device 10 in accordance with one embodiment of the present invention implanted in a patient 12. Implantable medical device 10 is contained within a hermetically-sealed, biologically inert outer shield or "can" 9. An implantable lead 14 is electrically coupled to implantable medical device 10 and extends into the patient's heart 16 via vein 18. The distal end of lead 14 includes one or more exposed conductive electrodes for receiving electrical cardiac signals and/or for delivering electrical stimuli to the heart 16. Lead 14 may be implanted with its distal end situated in the atrium or ventricle of heart 16.

Figure 2:
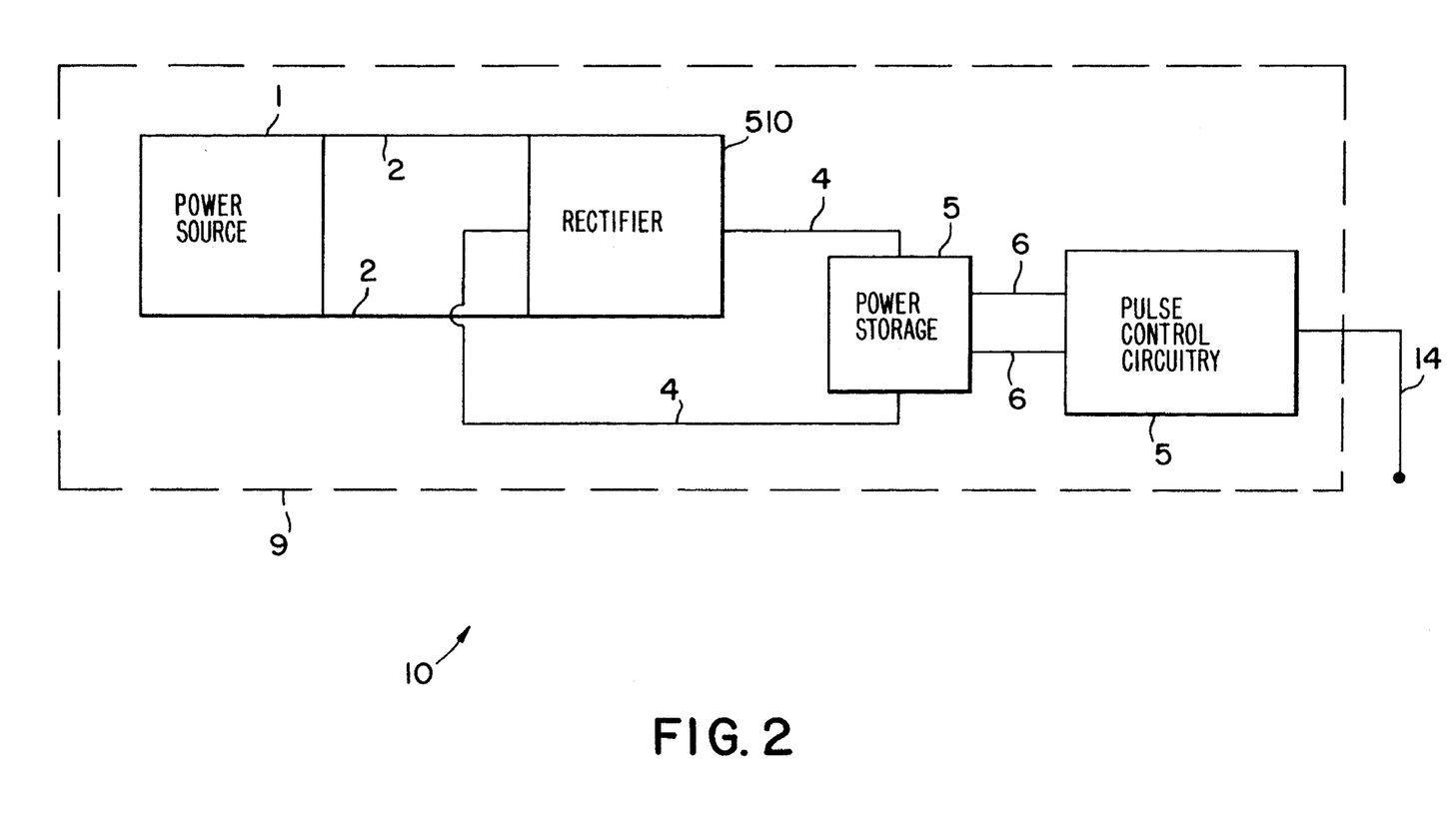
FIG. 2 is a block diagram of the implantable pulse generator of FIG. 1.

FIG. 2 is a block diagram of implantable medical device 10 of FIG. 1. As seen implantable medical device 10 has a power source 1 connected by conductors 2 to rectifier 510. Power source 1 in this embodiment is of the type which uses undirected movement of implantable medical device 10 (such as when a patient moves, walks or even breathes) to generate electrical energy. A suitable mechanism for power source 1 may be a device such as that described in the U.S. Pat. No. 4,644,246 of Knapen entitled "Electric Power Supply System for Portable Miniature Size Power Consuming Devices." As discussed in more detail below, the electrical energy generated by power source 1 is an A.C. electrical signal. Rectifier 510 rectifies or converts the A.C. signal into a D.C. signal. The operation and specific construction of rectifier 510 is depicted in FIGS. 5–10 discussed below. Rectifier 510, in turn, is connected to power storage 3 by conductors 4. Power storage 3 may be any acceptable device, such as a voltage regulator and battery or capacitor or any acceptable combination. Power storage 3 is connected to pulse control circuitry 5 by conductors 6.

Figure 3:
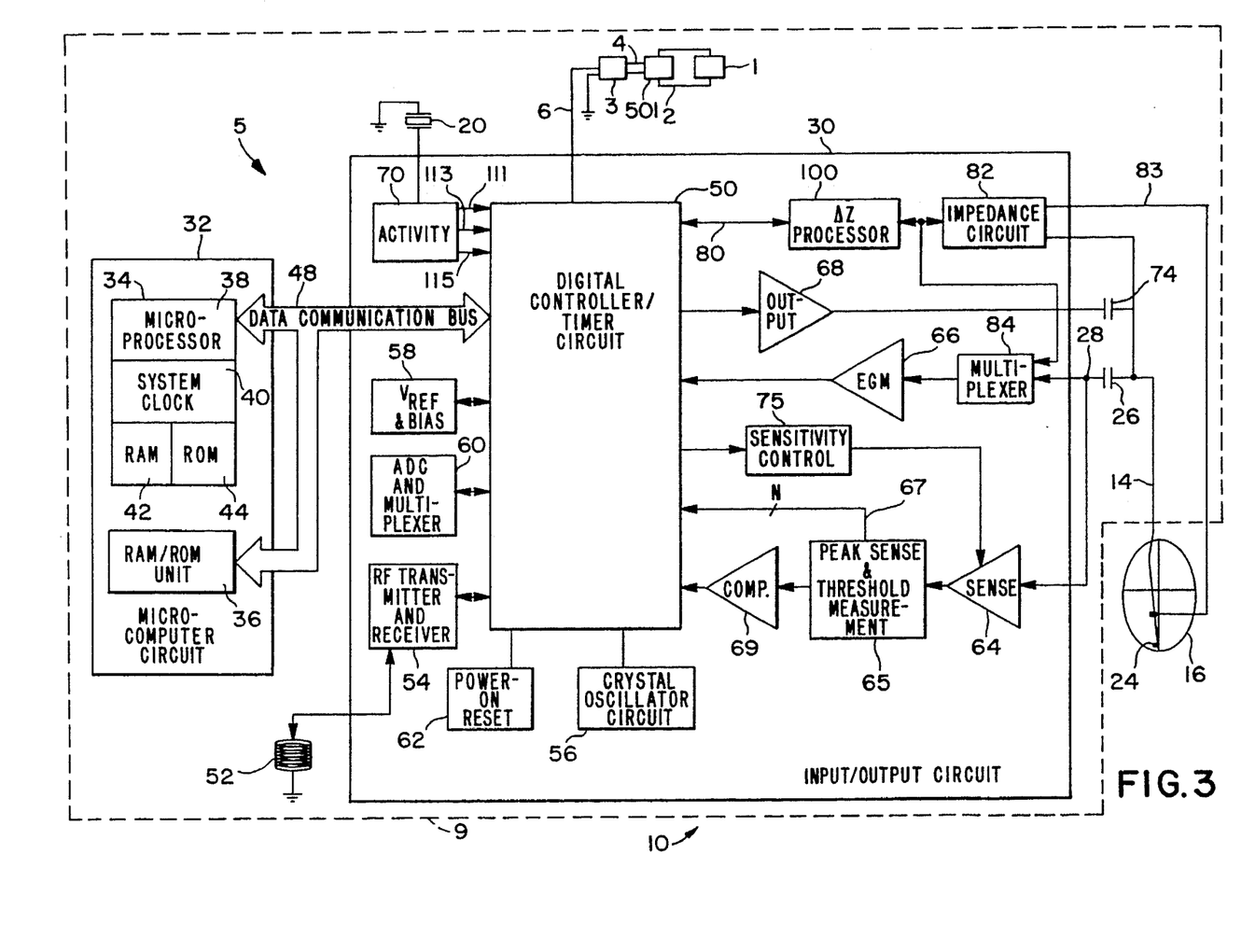
FIG. 3 is a block diagram of functional components of the implantable pulse generator of FIG. 2.

FIG. 3 is a block diagram of functional components of the implantable pulse generator used in the implantable medical device 10 of FIG. 2. Implantable medical device 10 includes an activity sensor 20, which may be, for example, a piezoelectric element bonded to the inside of the implantable pulse generator's shield. Activity sensor 20 provides a sensor output which varies as a function of a measured parameter that relates to the metabolic requirements of patient 12.

Implantable medical device 10 of FIG. 3 is programmable by means of an external programming unit (not shown in the FIGS.) One such programmer suitable for the purposes of the present invention is the Medtronic Model 9790 programmer. The programmer is a microprocessor device which provides a series of encoded signals to implantable medical device 10 by means of a programming head (not shown in the FIGS.) which transmits radio-frequency (RF) encoded signals to implantable medical device 10 according to a telemetry system.

Implantable medical device 10 is electrically coupled via a pacing lead 14 to a patient's heart 16. Lead 14 includes an intracardiac tip electrode 24 located near its distal end and positioned within the right ventricular (RV) or right atrial (RA) chamber of heart 16. Lead 14 is a bipolar electrode, as is well known in the art. Of course other types of leads, such as unipolar endocardial or epicardial, may also be used.

Lead 14 is coupled through input capacitor 26 to node 28 and to input/output terminals of an input/output circuit 30. Activity sensor 20 is bonded to the inside of the implantable pulse generator's outer protective shield. As shown in FIG. 3, the output from activity sensor 20 is coupled to input/output circuit 30, and in particular to activity circuit 70 described below.

Input/output circuit 30 contains the analog circuits for interface to the heart 16, activity sensor 20, antenna 52, as well as circuits for the application of stimulating pulses to heart 16 to control its rate as a function thereof under control of the software-implemented algorithms in a microcomputer circuit 32. Taken together input/output circuit 30 and microcomputer circuit 32 constitute pulse control circuitry 5 depicted in FIG. 2.

Microcomputer circuit 32 comprises an on-board circuit 34 and an off-board circuit 36. On-board circuit 34 includes a microprocessor 38, a system clock circuit 40, and on-board RAM 42 and ROM 44. In the presently disclosed embodiment of the invention, off-board circuit 36 includes a RAM/ROM unit. On-board circuit 34 and off-board circuit 36 are each coupled by a data communication bus 48 to a digital controller/timer circuit 50. Microcomputer circuit 32 may be fabricated of a custom integrated circuit device augmented by standard RAM/ROM components.

Power is provided by a power source 1. As seen best in FIG. 2, power source 1 is connected through conductors 2 to rectifier 510. Rectifier 510, in turn, is connected through conductors 4 to power storage 3.

Antenna 52 is connected to input/output circuit 30 for purposes of uplink/downlink telemetry through RF transmitter and receiver unit 54.

A crystal oscillator circuit 56, typically a 32,768-Hz crystal-controlled oscillator, provides main timing clock signals to digital controller/timer circuit 50. V REF & Bias circuit 58 generates stable voltage reference and bias currents for the analog circuits of input/output circuit 30. An analog-to-digital converter (ADC) and multiplexer unit 60 digitizes analog signals and voltage to provide "real-time" telemetry intracardiac signals and battery end-of-life (EOL) replacement function. DELTA Z Processor 100 is utilized in conjunction with output signals from impedance sensors. A power-on-reset (POR) circuit 62 functions as a means to reset circuitry and related functions to a default condition upon detection of a low battery condition, which will occur upon initial device power-up or will transiently occur in the presence of electromagnetic interference, for example.

The operating commands for controlling the timing of implantable medical device 10 are coupled by bus 48 to digital controller/timer circuit 50 wherein digital timers and counters are employed to establish the overall escape interval of the implantable pulse generator, as well as various refractory, blanking, and other timing windows for controlling the operation of the peripheral components within input/output circuit 30.

Digital controller/timer circuit 50 is coupled to sensing circuitry including a sense amplifier 64, a peak sense and threshold measurement unit 65, and a comparator/threshold detector 69. Circuit 50 is further coupled to receive an output signal from an electrogram (EGM) amplifier 66. EGM amplifier 66 receives, amplifies and processes electrical signals provided from multiplexer 84. Multiplexer 84 receives a signal from 1 of 2 places: 1) electrode 24, lead conductor 14 and capacitor 26, this signal being representative of the electrical activity of the patient's heart 16; and 2) an impedance waveform resulting from operation of an impedance circuit 82 (to be hereinafter described in detail).

Sense amplifier 64 amplifies sensed electrical cardiac signals and provides this amplified signal to peak sense and threshold measurement circuitry 65, which provides an indication of peak sensed voltages and the measured sense amplifier threshold voltage on multiple conductor signal path 67 to digital controller/timer circuit 50. The amplifier sense amplifier signal is then provided to comparator/threshold detector 69. Sense amplifier 64 may correspond, for example, to that disclosed in U.S. Pat. No. 4,379,459 issued to Stein and incorporated herein by reference. Sense amplifier 64 sensitivity is control by sensitivity control 75. The electrogram signal developed by EGM amplifier 66 is used on those occasions when the implanted device is being interrogated by an external programmer, not shown, to transmit by uplink telemetry a representation of the analog electrogram of the patient's electrical heart activity, such as described in U.S. Pat. No. 4,556,063, issued to Thompson et al. and incorporated herein by reference. As previously noted, EGM amplifier 66 also selectively receives an impedance waveform which may be transmitted by uplink telemetry to an external programmer.

An output pulse generator 68 provides pacing stimuli to the patient's heart 16 through coupling capacitor 74 in response to a pacing trigger signal developed by digital controller/timer circuit 50 each time the escape interval times out, or an externally transmitted placing command has been received, or in response to other stored commands as is well known in the pacing art. Output amplifier 68 may correspond generally to the output amplifier disclosed in U.S. Pat. No. 4,476,868 issued to Thompson and incorporated herein by reference.

While specific embodiments of input amplifier 64, output amplifier 68, and EGM amplifier 66 have been identified herein, this is done for the purposes of illustration only. The specific embodiments of such circuits are not critical to the present invention so long as they provide means for generating a stimulating pulse and provide digital controller/timer circuit 50 with signals indicative of natural and/or stimulated contractions of the heart.

Digital controller/timer circuit 50 is coupled to activity circuit 70 for receiving, processing, and amplifying signals received from activity sensor 20 by conductors 111, 113 and 115. Digital controller/timer circuit 50 is also coupled, via line 80 to a DELTA Z Processor circuit 100, which in turn is coupled to an impedance circuit 82. Impedance circuit 82 is coupled directly to pacing lead 14 by conductor 83. Impedance circuit 82 measures cardiac impedance by outputting periodic biphasic current pulses on pacing lead 14, and then sensing the resulting voltages. The resulting voltages are sensed and demodulated in an AC-coupled manner, to generate a voltage waveform (hereinafter "impedance waveform") which reflects changes in impedance (i.e., with baseline impedance substrated). The utilization of an impedance sensor of this type in a cardiac implantable pulse generator is the subject of the above-reference U.S. Pat. No. 4,702,253 to Nappholz et al. and incorporated herein by reference. The measured impedance changes will be related to respiratory changes in frequency and magnitude. The analog impedance waveform is scaled and filtered in impedance circuit 82, and the resulting waveform provided to DELTA Z Processor 100 for conversion to digital format. Further details concerning the construction and operation of such an implantable pulse generator may be found in U.S. Pat. No. 5,271,395 entitled "Method and Apparatus for Rate-Responsive Cardiac Pacing" of Wahlstrand et al. and incorporated herein by reference.

Although the present invention has been illustrated in the context of a single-chamber implantable pulse generator, it is equally applicable in dual-chamber implantable pulse generators. Finally, although the present invention has been specifically depicted in the context of an implantable pulse generator which functions as a cardiac pacemaker, it should be understood to be used in its broadest sense, and includes, without limitation, defibrillators, cardioverters, cardiac assist systems, nerve stimulators as well as all other medical pulse generators.

DETAILED DESCRIPTION OF A WRISTWATCH FEATURING THE RECTIFIER CIRCUIT OF THE PRESENT INVENTION

Figure 4A:
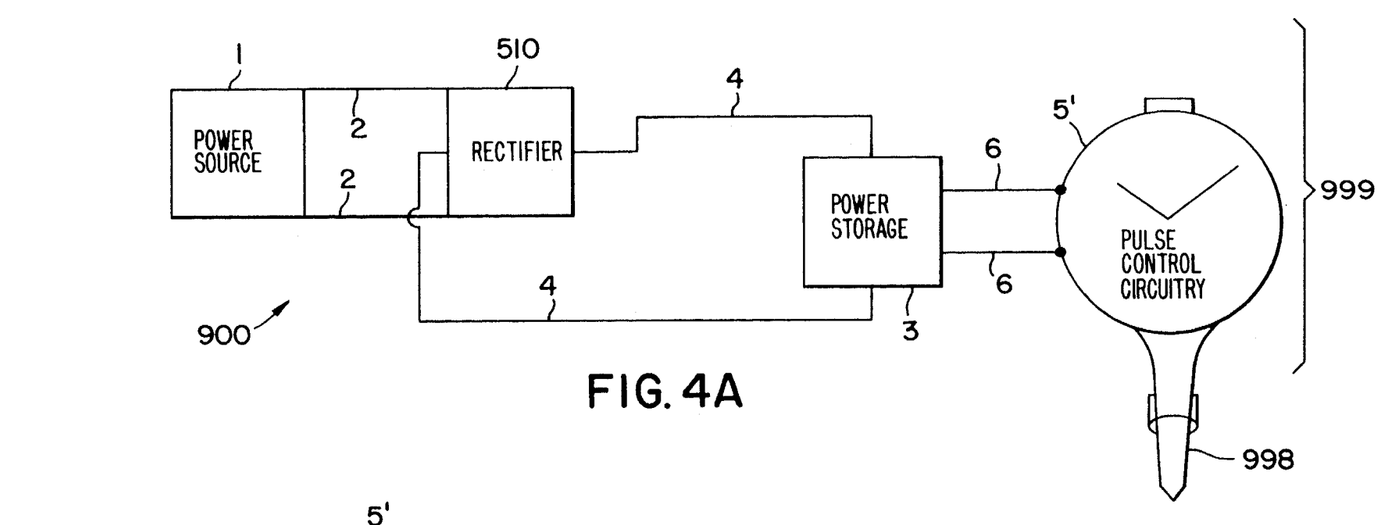
FIG. 4A is a schematic diagram of an alternate embodiment of the pulse generator featuring the full-wave rectifier circuit of the present invention employed within a wristwatch.

FIG. 4A is a block diagram of an alternate embodiment of the present invention in which full-wave rectifier 510 is used within a wristwatch 900. As seen wristwatch 900 has a power source 1 connected by conductors 2 to rectifier 510. Power source 1 uses undirected movement to generate electrical energy and may be the same as the power source described above. As discussed in more detail below, the electrical energy generated by power source 1 is an A.C. electrical signal. Rectifier 510 rectifies or converts the A.C. signal into a D.C. signal. The operation and specific construction of rectifier 510 is depicted in FIGS. 5–10 discussed below. Rectifier 510, in turn, is connected to power storage 3 by conductors 4. Power storage 3 may be any acceptable device, such as a voltage regulator and battery or capacitor or any acceptable combination. Power storage 3, in turn, is connected to pulse control circuitry 5' by conductors 6.

Figure 4B:
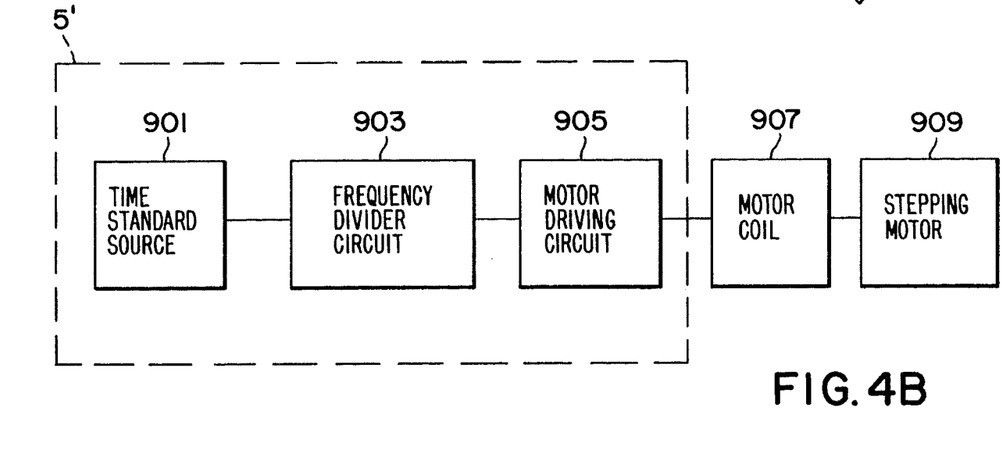
FIG. 4B is a block diagram of the pulse control circuitry used in the alternate embodiment of the pulse generator depicted in FIG. 4A.

FIG. 4B is a block diagram of the pulse control circuitry 5' used in the pulse generator depicted in FIG. 4A. As seen pulse control circuitry 5' include an time standard source 901. Time standard source 901 includes a crystal oscillator (not shown) and is connected, in turn, to frequency divider circuit 903 which, in turn, is connected to motor driving circuit 905. Motor driving circuit 905 drives motor coil 907 which, in turn, drives stepping motor 909 for rotating a pointer (not shown.) Further details of the construction and operation of a suitable pulse control circuitry 5' may be found in U.S. Pat. No. 4,788,669 entitled "Electronic Timepiece" issued to Kamiyama and U.S.. Pat. No. 4,615,625 entitled "Analog Electronic Timepiece" issued to Moriya each of which are incorporated herein by reference.

THE FULL-WAVE RECTIFIER CIRCUIT USED IN THE PRESENT INVENTION

As discussed above, the pulse generator of the present invention uses a full-wave rectifier circuit 510 to convert the A.C. signals output by power source 1 into D.C. signals suitable for use by pulse control circuitry 5 (or 5'.)

Figure 5:
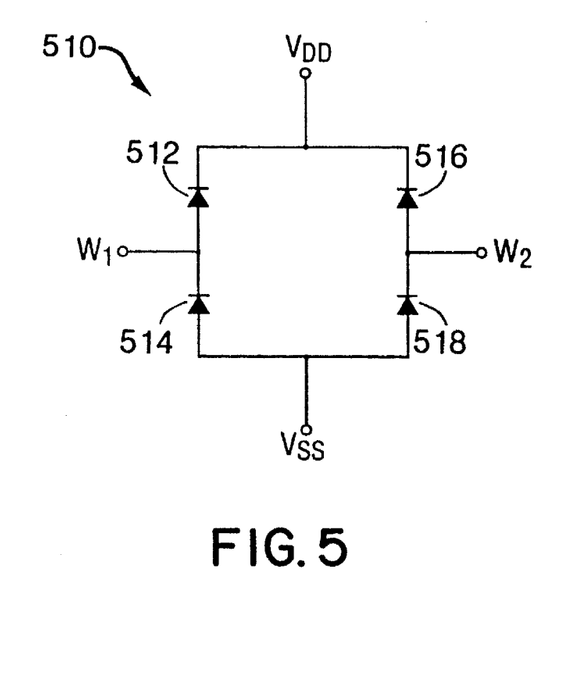
FIG. 5 is a simplified schematic diagram of a full-wave rectifier circuit in accordance with one embodiment of the present invention.

FIG. 5 shows a simplified schematic representation of a rectifier circuit 510. As seen rectifier circuit 510 comprises four diodes 512, 514, 516, and 518. As will be hereinafter described in greater detail, diodes 512, 514, 516, and 518 are not of the conventional P-N or Schottky type, but are instead implemented using field-effect transistors (FETs), in accordance with well-known practice in the circuit art.

Figure 6A:
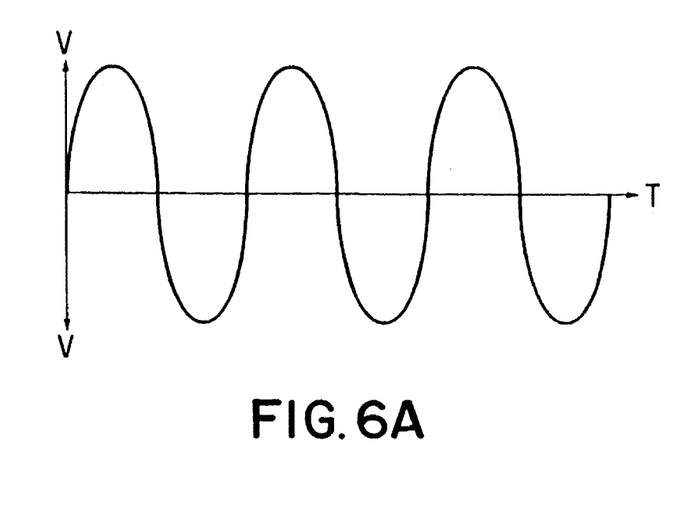
FIG. 6A is a plot of an oscillatory electrical waveform prior to rectification.
Figure 6B:
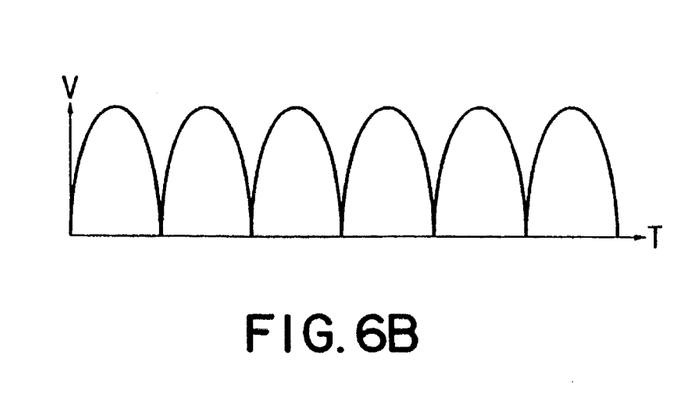
FIG. 6B is a plot of the electrical waveform after rectification.

Rectifier circuit 510 is configured to accept an oscillating (e.g., AC) signal applied between nodes designated W1 and W2 therein, and to produce a rectified (i.e., DC) signal between nodes designated $V_{DD}$ and $V_{SS}$. (As used herein, it will be assumed that the term "input signal" refers to a voltage differential established between the first and second input terminals W1 and W2, and that "output signal" refers to a voltage differential established between output terminals $V_{DD}$ and $V_{SS}$, in accordance with conventional circuit nomenclature.) Thus, for example, if the voltage waveform shown in FIG. 6A were applied between the W1 and W2 nodes, the resulting waveform as observed between the $V_{DD}$ and $V_{SS}$ nodes would appear as shown in FIG. 6B.

Figure 7:
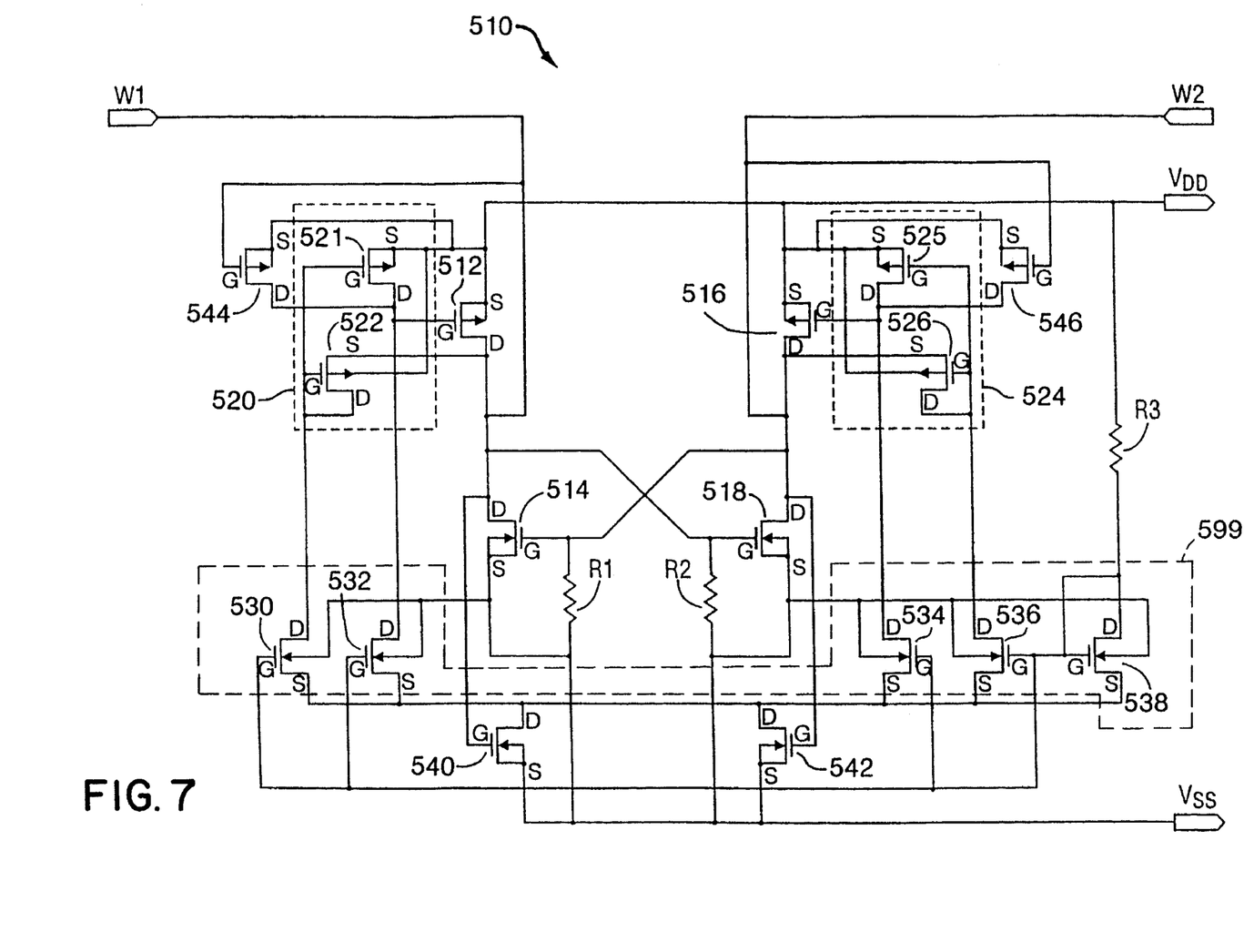
FIG. 7 is a more detailed schematic diagram of the rectifier circuit from FIG. 5.

As previously noted, diodes 512, 514, 516, and 518 in rectifier circuit 510 are implemented using FETs, which operate essentially as switches which turn on or off depending upon the voltage applied to their control inputs (gates). In particular, rectifier 510 is preferably implemented on an integrated circuit ("IC") as shown in the more detailed schematic diagram of FIG. 7. As shown in FIG. 7, diodes 512 and 516 are implemented using P-channel FETs, while diodes 514 and 518 are implemented using N-channel FETs. (In FIG. 7, the gate, source, and drain of each FET shown therein is identified with a "G," "S," and "D," respectively. In the following description, reference will be made, for example, to "the gate of FET 512," it being understood that this refers to the gate terminal of FET 512 identified with a "G".)

FIG. 7 shows that rectifier 510 further includes, among other elements, two voltage sensing differential amplifiers designated with reference numerals 520 and 524. Voltage-sensing differential amplifier 520, comprising two P-channel FETs 521 and 522, is associated with FET/diode 512, while voltage-sensing differential amplifier 524, comprising two P-channel FETs 525 and 526, is associated with FET/diode 516. Several other FETs, identified with reference numerals 530, 532, 534, 536, 538, 540, 542, 544, and 546, and three resistors R1, R2, and R3, are also included in rectifier circuit 510. The function of these additional elements will be described hereinbelow in greater detail.

As noted with reference to FIG. 5, rectifier circuit 510 is designed to receive an input signal between nodes W1 and W2. For example, W1 and W2 may be connected to the output terminals of an AC generator, such as a generator like that disclosed in U.S. Pat. No. 4,644,246 to Knapen, discussed below, as well as the relatively low-voltage generator which is described in Shouichi Nagao et al.; "A Study of the Automatic Generation System -Improvement of the Total System Performance;" Communication 33, 4th Congress European de Chronometrie, Oct. 29–30, 1992. The Nagao et al. reference describes a very small generator-like device including a rotary dead-mass, for converting relatively undirected movement, such as the movement of a watch-wearer's arm, into rotational motion usable to turn the armature of a dynamo for generating an AC electrical signal.

When an AC signal (such as that depicted in FIG. 6A) is applied between nodes W1 and W2 of rectifier circuit 510, during one phase of the signal the voltage on W1 will be positive and the voltage on W2 will be negative with respect to ground, while during the other phase of the signal the voltage on W2 will be positive and the voltage on W1 will be negative with respect to ground. (For the purposes of the following description, it will be assumed that $V_{SS}$ is at ground, while $V_{DD}$ is a positive voltage.)

As shown in FIG. 7 the gates of FETs 514 and 518 are coupled to $V_{SS}$ via resistors R1 and R2, respectively, and are further cross-coupled to the drains of each other (i.e., the gate of FET 514 is coupled to the drain of FET 518, and vice versa.) The drain of FET 514 is coupled to the W1 node, and the drain of FET 518 is coupled to the W2 node. The sources of FETs 514 and 518 are coupled directly to the $V_{SS}$ node. In addition, the drain of FET 514 and gate of FET 518 are coupled to the drain of FET 512, while the drain of FET 518 and the gate of FET 514 are coupled to the drain of FET 516. The sources of FETs 512 and 516 are each coupled to the $V_{DD}$ node.

For the purposes of the following description, it will be assumed that initially there is no voltage differential between nodes W1 and W2, and also that there is no voltage differential between nodes $V_{DD}$ and $V_{SS}$. In this case, FETs 514 and 518 will be turned off, since their gates are coupled, via resistors R1 and R2, respectively, to $V_{SS}$. When an AC signal such as depicted in FIG. 6A is applied between nodes W1 and W2, initially the voltage on node W1 (which is coupled to the drain of FET 514 and to the gate of FET 518) will begin to increase, turning on FET 518. Also, due to the connection between the drain of FET 514 and the gate of a FET 540, FET 540 is turned on in response to a rising W1 voltage, coupling the sources of FETs 530, 532, 534, 536 and 538 to $V_{SS}$.

In accordance with one aspect of the presently disclosed embodiment of the invention, FETs 530, 532, 534, 536, and 538 function as a bias circuit 599, providing current to differential amplifiers 520 and 524. Current is injected into bias circuit 599 from $V_{DD}$ through diode-connected FET 38, which operates as a current mirror. As shown in FIG. 7, the gates of FETs 530 and 532 are commonly connected to the gate and drain of current mirror/FET 538. The sources of FETs 530 and 532 are also tied together, as noted above, and are coupled to $V_{SS}$ via FET 540 in response to a positive voltage on node W1. Likewise, the gates of FETs 534 and 536 are commonly coupled to the gate and drain of FET 538, and the sources of FETs are tied together and coupled to $V_{SS}$ via FET 542 in response to a positive voltage on node W2.

In the presently preferred embodiment of the invention, the physical dimensions of FETs 530 and 532 are such that for a given common gate voltage and source voltage, the current through FET 530 is greater than that through FET 532. In particular, in the presently disclosed embodiment, FET 530 has (w/l) dimensions of 20-μ by 15-μ, whereas FET 532 has dimensions of 20-μ by 10-μ. Thus, the current through FET 530 is approximately 50% greater than that through FET 532, for a given gate voltage. There is a similar relationship between FETs 534 and 536. That is, the dimensions of FET 536 relative to FET 534 are such that approximately 50% more current flows through FET 536 than through FET 534, given common gate and source connections.

As shown in FIG. 7, the drain of FET 530 is tied to the gates of FETs 521 and 522 and the drain of FET 522, while the drain of FET 532 is died to the drain of FET 521, and to the gate of FET 512. Still assuming that the input voltage on node W1 initially rises, when the voltage on W1 nears $V_{DD}$, FETs 521 and 522 in sense amplifier 520 will have unequal gate voltages, due to the unequal currents through FETs 530 and 532. Those of ordinary skill in the art will appreciate that, given their interconnection, FETs 521 and 522 operate as a source-connected differential amplifier to sense the difference between the voltages on nodes W1 and $V_{DD}$. In particular, the voltage on node W1 must be only slightly (i.e., 10-to 15-mV or so) greater than the voltage on node $V_{DD}$ to reach an equilibrium wherein FET 521 begins to turn off. At this point, conduction through FET 532 discharges the gate of FET 512 to $V_{SS}$ and turns FET 512 on. FET 518 is also on at this point, due to the interconnection of the drain of FET 512 to the gate of FET 518. As a result, rectifier 510 begins operating as a bridge, with a current path established through FET 518 between node W2 and node $V_{SS}$, and a current path established through FET 512 between node W1 and node $V_{DD}$.

Those of ordinary skill in the art will appreciate that the small threshold voltage (10- to 15-mV or so, as noted above) by which the W1 voltage must exceed $V_{DD}$ in order for FET 521 to turn off and FET 512 to turn on is substantially less than the typical 0.7-V threshold voltage of conventional diodes.

During a negative-going excursion of the voltage between nodes W1 and W2, the voltage on node W2 rises with respect to that on W1. The rising W2 voltage turns on FET 514, effectively grounding the gate of FET 518 and reducing the drain-to-source voltage of FET 514. This increases the drain voltage of FET 518. The increased drain voltage of FET 518 turns on FET 542, taking the source rail of FETs 530, 532, 534, 536 and 538 to $V_{SS}$. Again, FET 38 operates as a current mirror to inject current through FETs 530, 532, 534 and 536. As noted above, the relative physical dimensions of FETs 534 and 536, like those of FETs 530 and 532, are such that approximately 50% more current is conducted through FET 536 than through FET 534, for a given common gate voltage. Thus, as the voltage on node W2 nears that on node $V_{DD}$, FETS 524 and 526 will have unequal gate voltages.

The gate voltage of FET 526 must be slightly greater than the gate voltage of FET 525 in order for FETs 525 and 526 operating as a differential amplifier to reach an equilibrium state, wherein FET 525 begins to turn off. This occurs when the voltage on node W2 just exceeds $V_{DD}$. When FET 525 turns off, conduction through FET 534 discharges the gate of FET 516, turning FET 516 on and establishing a path between node W2 and node $V_{DD}$ (through FET 516) and a path between node W1 and node $V_{SS}$ (through FET 514).

Again, those of ordinary skill in the art will appreciate that the threshold voltage by which the voltage on node W2 must exceed $V_{DD}$ in order for FET 525 to turn off and FET 516 to turn on is substantially less than the 0.7-V threshold voltage of conventional diodes.

Summarizing the operation of rectifier 510 in accordance with the presently disclosed embodiment of the invention, a bias circuit 599 comprising FETs 530, 532,534, 536 and 538 responds to both positive and negative excursions of the input signal between nodes W1 and W2 to activate a voltage sensing differential amplifier (differential amplifier 520 for positive excursions of the input signal, and differential amplifier 524 for negative excursions of the input signal). When so activated, each voltage sensing differential amplifier 520 and 524 detects when the absolute value of the magnitude of the input signal just exceeds $V_{DD}$. That is, differential amplifier 520 detects when the voltage on node W1 exceeds $V_{DD}$, while differential amplifier 524 detects when the voltage on node W2 exceeds $V_{DD}$.

For positive excursions of the input signal between nodes W1 and W2, differential amplifier 520 operates to turn the first diode/FET 512, as soon as the input signal exceeds $V_{DD}$ (i.e., without a 0.7 threshold voltage) thereby establishing a path between the W1 node and $V_{DD}$. At the same time, diode/FET 518 is rendered conductive and diode/FET 514 is rendered non-conductive by virtue of the coupling of the gate of FET 518 to the W1 node and the coupling of the gate of FET 514 to the W2 node. Thus, a path is established between the W2 node and $V_{SS}$.

For negative excursions of the input signal between nodes W1 and W2, differential amplifier 524 responds to the voltage on node W2 exceeding $V_{DD}$ to render diode/FET 516 conductive, establishing a path between node W2 and $V_{DD}$. At the same time, diode/FET 514 is rendered conductive and diode FET 518 is rendered non-conductive by virtual of the coupling of the gate of diode/FET 514 to the W2 node and the coupling of the gate of diode/FET 518 to the W1 node. Thus a path is established between the W1 node and $V_{SS}$.

In accordance with one important aspect of the present invention, the bias circuit 599 comprising FETs 530, 532, 534, 536 and 538 operates to provide current to one of the differential amplifiers 520 and 524. In this way, the effective "threshold voltage" of the diode/FETs 512 and 516 is minimized, since one of FETs 512 and 516 will be turned on as soon as the absolute value of the magnitude of the input signal exceeds $V_{DD}$. At the same time, however, the bias circuit 599 draws relatively minimal current (on the order of a few μ-Amps), and only when a non-zero input signal is applied to rectifier 510 (i.e., only when rectifier 510 is active).

Two additional P-type FETs, designated with reference numerals 544 and 546 in FIG. 7, are provided in order to prevent leakage of rectifier 510 when no input signal is applied. As noted above, the bias circuit 599 comprising FETs 530, 532, 534, 536 and 538 is activated only when an input signal (either positive or negative) is present between nodes W1 and W2. As a result, the differential amplifiers 520 and 524 do not function when no input signal is present. Since differential amplifiers 520 and 524 are coupled to the gates of diode/FETs 512 and 516, respectively, this means that when no input signal is applied to rectifier 510, neither sense amplifier 520 nor sense amplifier 524 is operable to turn on or off the diode/FET with which it is associated. This leaves the gates of diode/FETs 512 and 516 effectively "floating," leading to the possibility that either or both of FETs 512 and 516 could be rendered conductive, allowing for leakage between $V_{DD}$ and $V_{SS}$ through diode/FET 512 and resistor R2, or through diode/FET 516 and resistor R1.

To overcome this problem, FETs 544 and 546 are included in rectifier 510 to affirmatively hold diode/FETs 512 and 516 off when no input signal is applied between nodes W1 and W2. FET 544 has its gate coupled to node W1, its source connected to $V_{DD}$, and its drain connected to the gate of diode/FET 512. FET 546 has its gate coupled to W2, its source coupled to $V_{DD}$, and its drain connected to the gate of diode/FET 516. When there is no input signal between nodes W1 and W2, FET 544 applies the $V_{DD}$ voltage to the gate of diode/FET 512, turning diode/FET 512 off. Similarly, FET 546 applies the $V_{DD}$ voltage to the gate of diode/FET 516, turning diode/FET 516 off, when no input signal is applied between nodes W1 and W2. In this way, FETs 544 and 546 operate as clamping circuits to prevent activation of FETs 512 and 516 in the absence of an input signal between nodes W1 and W2.

Resistors R1 and R2 function to balance the gate voltages of FETs 514 and 518 when those FETs are turned off (i.e., when no input signal is applied between nodes W1 and W2).

The following Table 1 summarizes the device type and size for each of the circuit components in the circuit of FIG. 7 (FET device sizes are (W/L)):

TABLE 1

| REFERENCE NO. IN FIG. 7 | DEVICE TYPE | DEVICE SIZE |
| --- | --- | --- |
| 512 | P-type FET | 5 m/1.5μ |
| 514 | N-type FET | 2 m/1.5μ |
| 516 | P-type FET | 5 m/1.5μ |
| 518 | N-type FET | 2 m/1.5μ |
| 521 | P-type FET | 20μ/5μ |
| 522 | P-type FET | 20μ/5μ |
| 525 | P-type FET | 20μ/5μ |
| 526 | P-type FET | 20μ/5μ |
| 530 | N-type FET | 20μ/15μ |
| 532 | N-type FET | 20μ/10μ |
| 534 | N-type FET | 20μ/15μ |
| 536 | N-type FET | 20μ/10μ |
| 538 | N-type FET | 20μ/10μ |
| 540 | N-type FET | 20μ/1.5μ |
| 542 | N-type FET | 20μ/1.5μ |
| 544 | P-type FET | 20μ/1.5μ |
| 546 | P-type FET | 20μ/1.5μ |
| R1 | resistor | 100-kΩ |

TABLE 1-continued

| REFERENCE NO. IN FIG. 7 | DEVICE TYPE | DEVICE SIZE |
| --- | --- | --- |
| R2 | resistor | 100-kΩ |
| R3 | resistor | 2-MΩ |

Figure 8:
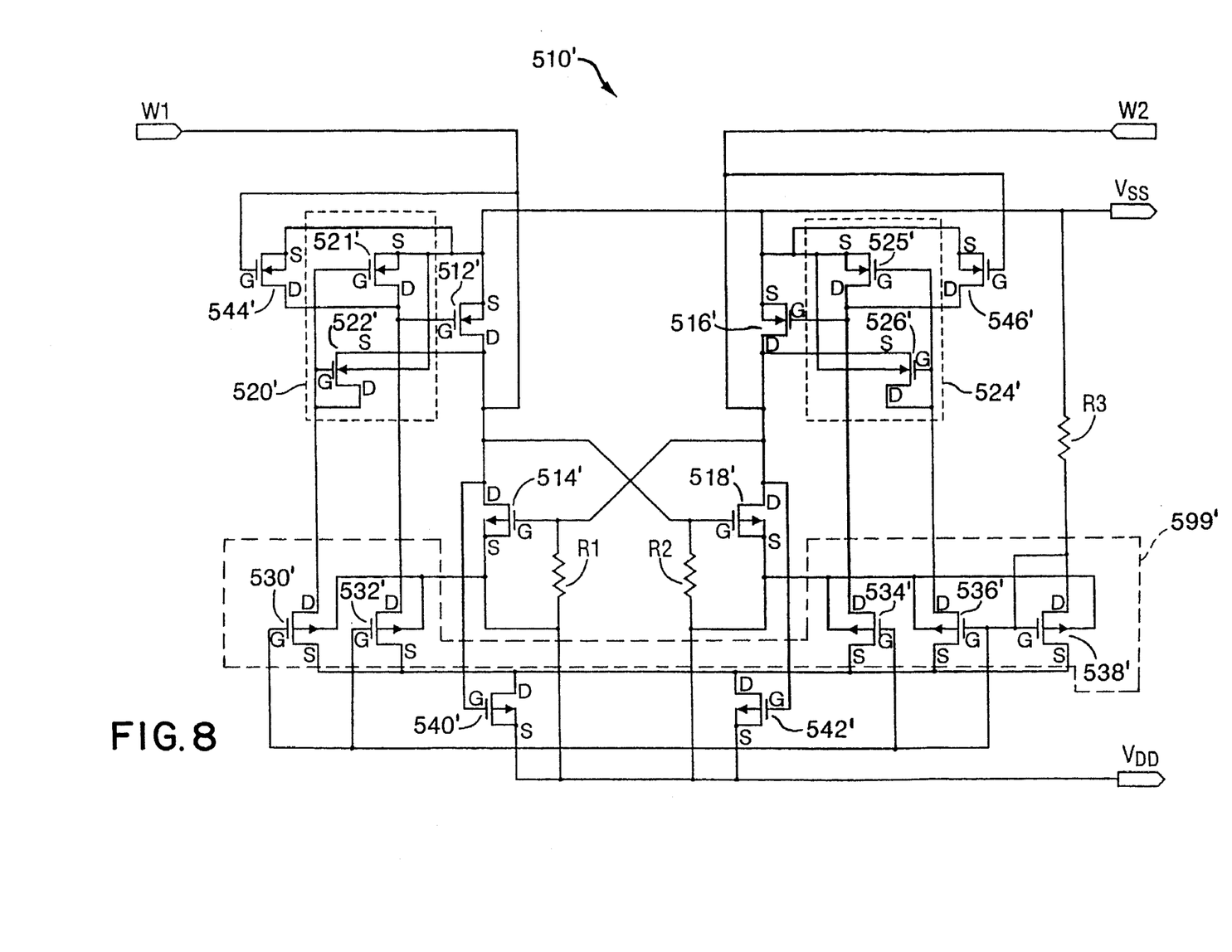
FIG. 8 is a schematic diagram of a full-wave rectifier circuit in accordance with an alternative embodiment of the invention.

An alternative embodiment of the invention, which is in some respects preferable to the embodiment that has been described hereinabove with reference to FIG. 7, is shown in FIG. 8. The rectifier 510' of FIG. 8 is substantially identical in configuration to that of FIG. 7, except that all N-type FETs in the embodiment of FIG. 7 are P-type in the embodiment of FIG. 8, and all P-type FETs in the embodiment of FIG. 7 are N-type in the embodiment of FIG. 8. In FIG. 8, a "'" has been added to each reference numeral from FIG. 7; thus, for example, the FET in FIG. 8 that corresponds with FET 512 in FIG. 7 is designated with 512' in FIG. 8, and so on.

Those of ordinary skill in the art will be familiar with the complementary relationship between N-type and P-type FETs, and it is thus believed that a detailed explanation of the operation of the rectifier 510' of FIG. 8 is not necessary given the detailed explanation of the operation of the circuit of FIG. 7. In general, in the implementation of FIG. 8, FET 518' is turned on by a negative excursion of the input signal between nodes W1 and W2, whereas FET 518 in the embodiment of FIG. 7 turns on in response to a positive excursion of the input signal. Likewise, the negative excursion of the input signal causes FET 528' in the embodiment of FIG. 8 to turn on, shorting the drains of bias circuit 599' comprised of transistors 530', 532', 534', 536' and 538' to $V_{DD}$.

One reason that the implementation of FIG. 8 is deemed preferable to that of FIG. 7 is that N-type FETs are known to have a lower on-resistance than P-type FETs for a given size device. Thus, to have a P-type FET and an N-type FET in states of equal conductivity given identical bias conditions and gate voltages, the P-type FET must be physically larger than the N-type FET. In rectifier circuit 510 of FIG. 7, it is the P-type FETs 512 and 516 which are driven by differential amplifiers 520 and 524, respectively. However, since the P-type FETs must be larger, and as a result have larger capacitances, it may be preferable to have differential amplifiers 520' and 524' drive N-type FETs, as in the alternative implementation shown in FIG. 8.

In either of the embodiments of FIGS. 7 and 8, rectifiers 510 and 510' draw a small amount of current from the $V_{DD}$ and $V_{SS}$ terminals to begin operating in their electronically switched modes (i.e., in the modes in which sense amplifiers 520 and 524 are dynamically biased to turn on diode/FETs 512 and 514 immediately upon the rising of the input voltage above $V_{DD}$ (or below $-V_{DD}$)). The amount of current drawn, however, is minimal compared with the amount of current returned as a result of operation of rectifier 510. Rectifier 510 (or 510') may draw, for example, a few μ-Amps from the $V_{DD}/V_{SS}$ terminals, but return tens of milliamps. In addition, current is drawn only when rectifier 510 (or 510') is active.

Figure 9:
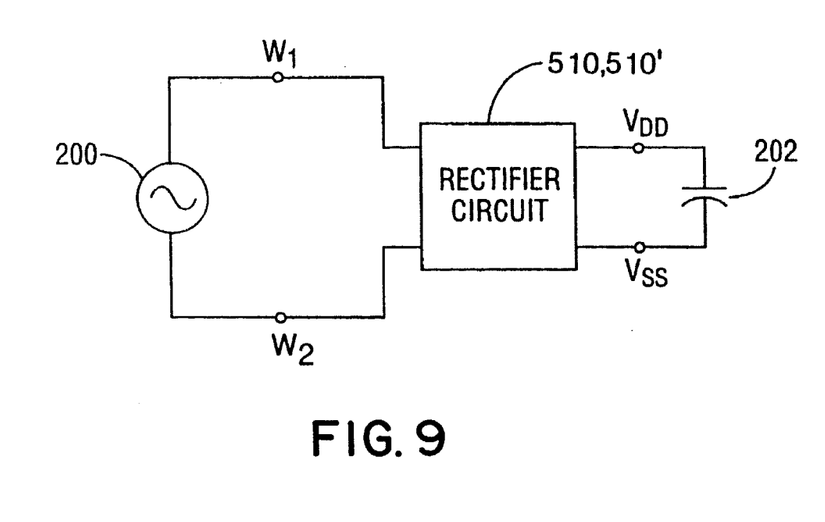
FIG. 9 is a schematic diagram of a circuit including a voltage source, the rectifier from FIG. 7, and an energy storage device.

Turning now to FIG. 9, there is shown an exemplary application of rectifier 510 (or rectifier 510') in accordance with the present invention. In the circuit of FIG. 9, rectifier 510 (or rectifier 510') is coupled to the output terminals of a voltage source 200 which, in one application, is a small generator assembly suitable for inclusion in a wristwatch or the like. One generator which may be used in such an application is one such as that disclosed in Shouichi Nagas et al., "A Study of the Automatic Generation System - Improvement of the Total System Performance;" Communication 33, 4th Congress European de Chronometrie, Oct. 29–30, 1992, discussed above. An additional embodiment of generator which may be used as a voltage source 200 is the so-called Kinetron dynamo, manufactured and commercially available from Kinetron, B. V., Tilburg, The Netherlands. The Kinetron dynamo is described in detail in U.S. Pat. No. 4,644,246 to Knapen, entitled "Electric Power Supply System for Portable Miniature-Size Power Consuming Devices" discussed above.

In accordance with the '246 patent's disclosure, the Kinetron dynamo includes a multi-polar rotor wheel having permanently magnetized poles, and a stator having one or more windings. An eccentric dead-weight mass is mounted about the same axis as the stator and rotor wheel. As the eccentric mass rotates, its rotational energy is stored as tension that is gradually built up in a leaf spring. The leaf spring allows the mass to rotate in only a single direction, until sufficient energy is stored in the spring cause the mass to be released. The energy stored in the leaf spring is then converted into a short burst of accelerated rotation of the rotor wheel.

Figure 10A:
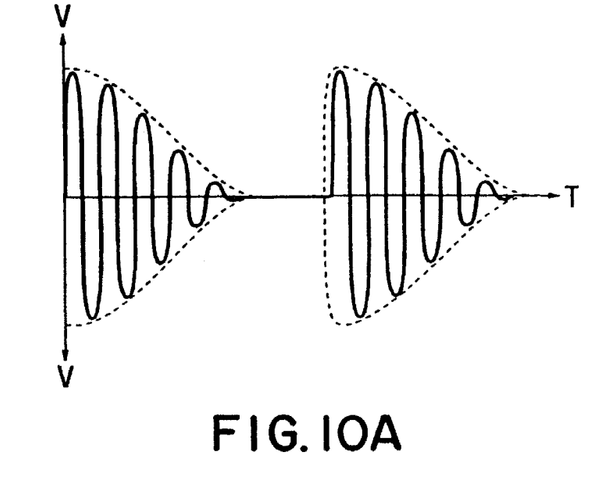
FIG. 10A is a plot of an oscillatory, damped sinusoidal electrical energy burst generated by the voltage source from FIG. 9.
Figure 10B:
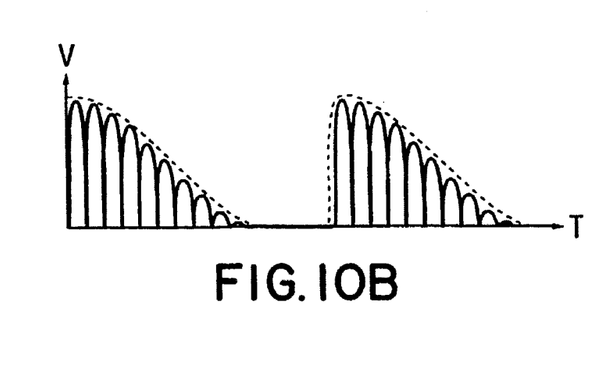
FIG. 10B is a plot of the energy burst from FIG. 10A after rectification by the rectifier from FIG. 7.

The Kinetron dynamo is adapted to convert relatively undirected motion, such as the movement of a wristwatch wearer's arm, into rotary motion of the rotor wheel, such that an oscillating (AC) electrical signal is generated. The rotor wheel is turned by the release of the tension in the spring at rates up to 15- to 20,000 RPM, for 200-mSec or so. The burst of energy oscillates at frequencies on the order of 2- to 3-kHz, with current levels of 5- to 10-mAmps or so, and with maximum peak-to-peak voltages on the order of 7-V or so. Each burst takes the form of a damped sinusoidal waveform, and these bursts can occur one or two times a second in normal operation. In illustration of the output from the Kinetron dynamo is depicted in FIG. 10A.

It is believed that rectifier 510 is particularly appropriate for rectification of the relatively high frequency and relatively low current energy bursts generated by such a dynamo. As shown in FIG. 9, the W1 and W2 inputs to rectifier 510 may be coupled to the output from voltage source 200, and the $V_{DD}$ and $V_{SS}$ outputs from rectifier 510 may be coupled to an energy storage device 202, which is represented in FIG. 9 as a capacitor, but may also be a battery or the like. The arrangement depicted in FIG. 9 would be advantageously useable in a wristwatch or similar small, battery-powered device.

In one embodiment, energy storage device 202 is a high-power, high energy density electrochemical double-layer capacitor. (Such a capacitor, sometimes referred to as a "supercap" is described in greater detail in Glenda Derman, Electronic Engineering Times, "Electrochemical Caps Diversify" Jun. 20, 1994, pp. 58–61) Supercaps are known to have an equivalent series resistance (ESR) on the order of 50-Ω or so. Whereas in some applications this ESR might be undesirable, such an ESR is actually beneficial to the practice of the present invention. As described above, rectifier circuit 510 operates to generate current from its $V_{DD}$ node, which current can be used, as in FIG. 9, to charge an energy storage device. As soon as the current from rectifier 510 (or 510') is applied to supercap 202, a voltage will be developed on the $V_{DD}$ node, due to the ESR of the supercap 202. This means that rectifier 510 will be instantly activated into its electronically switched mode, wherein the dynamic biasing of sense amplifiers 520 and 524 occurs. For lower-impedance energy storage devices used in place of supercap 202 in the circuit of FIG. 9, the $V_{DD}$ voltage may be established relatively more slowly; this phenomenon, however, is limited in extent, and is negligible in all but the lowest voltage operation of rectifier 510.

From the foregoing detailed description of specific embodiments of the invention, it should be apparent that a movement powered pulse generator has been disclosed, The specific embodiments illustrated included a cardiac pacemaker and a wristwatches. The present invention particularly concerns such a pulse generator which features a full-wave rectifier circuit which has dynamic bias. Although specific embodiments of the invention have been described herein, this has been done merely to illustrate the invention in various of its aspects, and is not intended to be limiting with respect to the scope of the invention. It is contemplated that various substitutions, alterations, and/or modifications, including but not limited to those specifically discussed herein, may be made to the disclosed embodiments without departing from the spirit and scope of the invention as defined in the appended claims. For example, specific FET sizes and types have been identified herein in connection with the disclosed embodiments of the invention, but those of ordinary skill in the art will appreciate that other device sizes and types may be specified for a given implementation of the invention, as a matter of routine circuit design.

What is claimed is:

1. An implantable pulse generator comprising:

a hermetically sealed can;

means for generating an AC signal from physical movement of a patient, the means for generating connected to the can;

means for rectifying the AC signal, the means for rectifying having first and second input terminals for receiving the AC electrical signal therebetween, a first differential sense amplifier connected to the first input terminal and a second differential sense amplifier connected to the second input terminal, first and second output terminals for presenting a rectified output signal therebetween, the means for rectifying further having means for dynamically biasing the first differential sense amplifier such that no bias current is applied to the first differential sense amplifier when no input signal is present and for dynamically biasing the second differential sense amplifier such that no bias current is applied to the second sense amplifier when no input signal is present;

an energy storage device connected to the output terminals;

means for sensing the electrical activity of a body organ connected to the energy storage device; and means for responding to the sensed electrical activity of a body organ connected to the means for sensing the electrical activity of a body organ, the means for responding delivering electrical stimuli to the body organ.

\* \* \* \* \*